US012400323B2

(12) United States Patent
Hall et al.

(10) Patent No.: US 12,400,323 B2
(45) Date of Patent: Aug. 26, 2025

(54) SYSTEM AND METHOD FOR ASSESSING BREAST CANCER RISK USING IMAGERY

(71) Applicant: iCAD, Inc., Nashua, NH (US)

(72) Inventors: Per Frans Leonard Hall, Stockholm (SE); Mikael Emil Dan Eriksson, Taby (SE); Kourosh Jafari-Khouzani, Nashua, NH (US); Senthil Periaswamy, Hollis, NH (US)

(73) Assignee: iCAD, Inc., Nashua, NH (US)

( * ) Notice: Subject to any disclaimer, the term of this patent is extended or adjusted under 35 U.S.C. 154(b) by 1034 days.

(21) Appl. No.: 17/632,559

(22) PCT Filed: Nov. 22, 2019

(86) PCT No.: PCT/US2019/062869
§ 371 (c)(1),
(2) Date: Feb. 3, 2022

(87) PCT Pub. No.: WO2020/107023
PCT Pub. Date: May 28, 2020

(65) Prior Publication Data
US 2022/0398721 A1 Dec. 15, 2022

Related U.S. Application Data

(60) Provisional application No. 62/770,958, filed on Nov. 23, 2018.

(51) Int. Cl.
*G16H 50/30* (2018.01)
*G06T 7/00* (2017.01)
*G16H 30/20* (2018.01)

(52) U.S. Cl.
CPC ........... *G06T 7/0012* (2013.01); *G16H 30/20* (2018.01); *G16H 50/30* (2018.01);
(Continued)

(58) Field of Classification Search
CPC .................................................. G06T 7/0012
See application file for complete search history.

(56) References Cited

U.S. PATENT DOCUMENTS

| 6,282,305 B1 | 8/2001 | Huo |
| 7,664,604 B1 | 2/2010 | Heine |

(Continued)

FOREIGN PATENT DOCUMENTS

| JP | 2008200482 | 9/2008 | |
| WO | WO-2017193059 A1 * | 11/2017 | ............ A61K 35/17 |
| WO | 2018042272 | 3/2018 | |

OTHER PUBLICATIONS

Eriksson et al., "A clinical model for identifying the short-term risk of breast cancer", Breast Cancer Research (2017) 19:29, DOI 10.1186/s13058-017-0820-y, 8 pages.

(Continued)

*Primary Examiner* — Di Xiao
(74) *Attorney, Agent, or Firm* — Loginov & Associates, PLLC; William A. Loginov

(57) ABSTRACT

This invention provides a system and method for assessing risk of a breast cancer diagnosis based upon imagery of tissue and (optionally) other patient-related factors. A CAD (or similar) system analyzes the imagery and generates a plurality of numerical feature values. An assessment module receives inputs from patient factors and history and computes the risk based upon the feature values and the patient factors and history. A masking module receives inputs from the patient factors and history, and computes the risk of having a cancer, which cancer is otherwise characterized by a low probability of detection, based upon the feature values and the patient factors and history. A recall module receives inputs from the assessment module and the masking assessment module, and generates a computer-aided indication of (Continued)

a clinical follow-up by the patient. Results of assessment(s) can be displayed to the clinician and/or patient using a graphical interface display.

20 Claims, 13 Drawing Sheets

(52) U.S. Cl.
CPC .............. *G06T 2200/24* (2013.01); *G06T 2207/10116* (2013.01); *G06T 2207/30068* (2013.01); *G06T 2207/30096* (2013.01)

(56) References Cited

U.S. PATENT DOCUMENTS

| | | | |
|---|---|---|---|
| 8,855,388 | B2 | 10/2014 | Wehnes |
| 9,361,683 | B2 | 6/2016 | Highnam |
| 2003/0174873 | A1 | 9/2003 | Giger |
| 2005/0049497 | A1 | 3/2005 | Krishnan |
| 2009/0232376 | A1 | 9/2009 | Raundahl |
| 2009/0324049 | A1* | 12/2009 | Kontos ............... A61B 6/5217 382/173 |
| 2010/0124364 | A1 | 5/2010 | Huo |
| 2011/0013819 | A1 | 1/2011 | Raundahl |
| 2014/0327702 | A1 | 11/2014 | Kreeger |
| 2015/0036906 | A1 | 2/2015 | Kim |
| 2015/0112705 | A1* | 4/2015 | Neville ................. G16H 50/30 705/2 |
| 2015/0148677 | A1* | 5/2015 | Mullick .................... G06T 7/13 600/443 |
| 2016/0066872 | A1 | 3/2016 | Kreeger |
| 2016/0110516 | A1* | 4/2016 | Ma ......................... G16H 50/30 705/2 |
| 2016/0110863 | A1 | 4/2016 | Heine |
| 2017/0091937 | A1* | 3/2017 | Barnes ................. G06V 10/771 |
| 2018/0260949 | A1 | 9/2018 | Kreeger |
| 2019/0065691 | A1* | 2/2019 | Erdmann ............... G16H 10/60 |
| 2019/0122397 | A1* | 4/2019 | Calhoun .............. G06T 7/0012 |
| 2020/0372649 | A1* | 11/2020 | Nakane ................ G06T 7/0014 |

OTHER PUBLICATIONS

Eriksson et al., "A comprehensive tool for measuring mammographic density changes over time", Breast Cancer Research and Treatment (2018) 169:371-379, https://doi.org/10.1007/s10549-018-4690-5.

Gastounioti et al., "Beyond breast density: a review on the advancing role of parenchymal texture analysis in breast cancer risk assessment", Breast Cancer Research (201) 18:91, DOI: 10.1186/s13058-016-0755-8.

Keller et al., "Breast Cancer Risk Prediction via Area and Volumetric Estimates of Breast Density", ADA Maidment, PR Bakic, and S. Gavenonis (Eds.): IWDM 2012, LNCS 7361, pp. 236-243.

NICE (National Institute for Health and Care Excellence), "Familial breast cancer: classification, care and managing breast cancer and related risks in people with a family history of breast cancer", Clinical Guideline, Published Jun. 25, 2013, 49 pages, www.nice.org.uk/guidance/cg164.

* cited by examiner

SYSTEM AND METHOD FOR ASSESSING BREAST CANCER RISK USING IMAGERY

FIELD OF THE INVENTION

This invention relates to systems and methods to determine risk for being diagnosed with a cancerous condition in (e.g.) the breast, based on imagery of breast tissue and other tissues, and more particularly to systems and methods that can also incorporate genetic risk variants, inherited risks, personal history, and/or lifestyle factors.

BACKGROUND OF THE INVENTION

Risk prediction models for breast cancer use lifestyle factors, family history of breast cancer, mammographic density, genetic determinants, or any combination of these factors to predict risk of developing the disease. Mammographic density is one of the strongest risk factors for breast cancer and consists of the radiographically dense fibroglandular part of the mammogram. Women with dense breasts have both an increased risk of breast cancer and a higher probability for a cancer being masked (undetected). Women with abnormal tissue changes in the breast have increased risk for later diagnosis of breast cancer. It is currently mandatory by law to report the level of mammographic density to a woman undergoing a mammography in 27 U.S. states, but there is no obligation to report the risk of breast cancer.

Current computer-aided detection (CAD) software applications/systems are designed to support radiologists at mammographic screening units in diagnosing early breast cancer. These systems and/or type(s) of software can indicate suspicious microcalcifications and masses. One such system is described in commonly assigned U.S. Pat. No. 8,855,388, entitled MICROCALCIFICATION DETECTION CLASSIFICATION IN RADIOGRAPHIC IMAGES, issued Oct. 2, 2014, the teachings of which are expressly incorporated herein by reference as useful background information. Briefly, this system operates on input digitized (e.g.) mammography image data of a breast, in which the digitized image is repeatedly convolved to form first convolved images. The first convolved images are convolved a second time to form second convolved images. Each first convolved image and the associated respective second convolved image represent a stage, and each stage represents a different scale or size of anomaly. As an example, the first convolution may utilize a Gaussian convolver, and the second convolution may utilize a Laplacian convolver, but other convolvers may be used. After being derived, the second convolved image from a current stage and the first convolved image from a previous stage are then used with a neighborhood median determined from the second convolved image from the current stage by a peak detector to detect peaks, or possible anomalies for that particular scale.

A study by Eriksson et al. (incorporated herein by reference as useful background information) shows that a CAD detection system could be used to extend risk models by including microcalcifications and masses as risk factors for later being diagnosed with breast cancer. See, in the attached Appendix, Mikael Eriksson, Kamila Czene, Audi Pawitan, Karin Leifland, Hatef Darabi and Per Hall, entitled *A clinical model for identifying the short-term risk of breast cancer*, Breast Cancer Research (2017) 19:29 (a study in association with Karolinska Institute of Stockholm, Sweden). This study compared women at highest mammographic density yielded a five-fold higher risk of breast cancer compared to women at lowest density. When adding suspicious lesions with microcalcifications and masses to the model, high-risk women had a nearly nine-fold higher risk of breast cancer than those at lowest risk. In the full model, taking HRT use, family history of breast cancer, and menopausal status into consideration, the area under the curve (AUC) reached 0.71. Notably, this study takes into account breast image data in determining risk. In this case, the image data associated with breast density and texture is employed. More particularly, the number of microcalcifications present in the left breast versus right breast is taken into account in the assessment. Images prior to diagnostic images are used to determine at-risk lesions in the breast.

There exist other models for determining breast cancer risk—for example the Tyrer-Cuzick, BOADICEA, and Gail models. These models do not take breast imagery for at-risk lesions into consideration. It is desirable to leverage the availability of high-resolution breast image information to improve the determination of a risk score in breast cancer screening.

SUMMARY OF THE INVENTION

This invention overcomes disadvantages of the prior art by providing an easily implementable prediction tool for individualized breast cancer screening without adding substantial cost or effort to the health care system, that can be based on detection of structures in the tissue, such as microcalcifications. Such microcalcifications can be based (e.g.) on detection of at-risk lesions. The characteristics of these detected structures can be optionally combined with risk factors, including, but not limited to, with mammographic density, genetic risk variants, inherited risks, comorbidities, hormonal and lifestyle factors. The process(or) employed includes a CAD (or similarly configured and functioning) computing system, based upon a deep learning, AI, neural network, and/or similar computing/data-handling arrangement, which can produce highly accurate features from acquired imagery. Notably, the CAD system for at-risk lesions is employed to augment and facilitate a prediction of risk of developing a disease (e.g. breast cancer) in addition to more traditional applications, in which the CAD is employed to diagnose existing conditions. More particularly, the acquired breast image data can provide additional image features that are, in turn, used to derive more informative predictive risk score models than previously employed microcalcifications and density (masses) measurements.

In an illustrative embodiment, a system and method for assessing risk of being diagnosed with cancer based upon imagery of tissue and (optionally) other patient-related factors is provided. A CAD (or similarly configured) system analyzes the imagery and generates a plurality of numerical feature values. An assessment module (optionally) receives inputs from patient factors and history and computes the risk based upon the feature values and the patient factors and history. A masking determination module receives inputs from the patient-related factors, and computes the risk of having a cancer, which cancer is otherwise characterized by a low probability of detection, based upon the feature values and the patient factors and history. A recall determination module receives inputs from the assessment module and the masking assessment module, and generates a computer-aided indication of a clinical follow-up by the patient. The assessment module can also receive score data from prior imagery of tissue for monitoring a therapy response by a clinician. Results of assessment(s) can be displayed to the clinician and/or patient using a graphical interface display. Illustratively, the assessment module receives score data from prior imagery of tissue that is verified to include cancer by a specialist. The assessment module also receives score data from prior imagery of tissue for monitoring a therapy response by a clinician. The patient-related factors can include at least one of (a) breast imagery, (b) percent tissue density, (c) density compactness, (d) age when the imagery is acquired, (e) BMI, (f) menopause status, (g) family history of cancer, (h) personal history of disease, (i) lifestyle, (j) genetic variants, and (k) information from prior health care examinations. Also, the assessment module can be arranged to determine cancer of a specific subtype or generalized breast cancer. The features are established based upon lesion candidates localized in the tissue by the CAD system. Additionally, the risk assessment module can employ breast side differences for microcalcifications, masses and the tissue density and/or can employ an interaction between tissue density and masses. A user interface output module that can provide a graphical display output of the risk versus a scale of risk values, the masking versus a scale of masking values, and/or a recall score. In various embodiments, the tissue is human breast tissue and the imagery is mammography imagery.

BRIEF DESCRIPTION OF THE DRAWINGS

The invention description below refers to the accompanying drawings, of which.

DETAILED DESCRIPTION

I. System Overview

Figure 1:
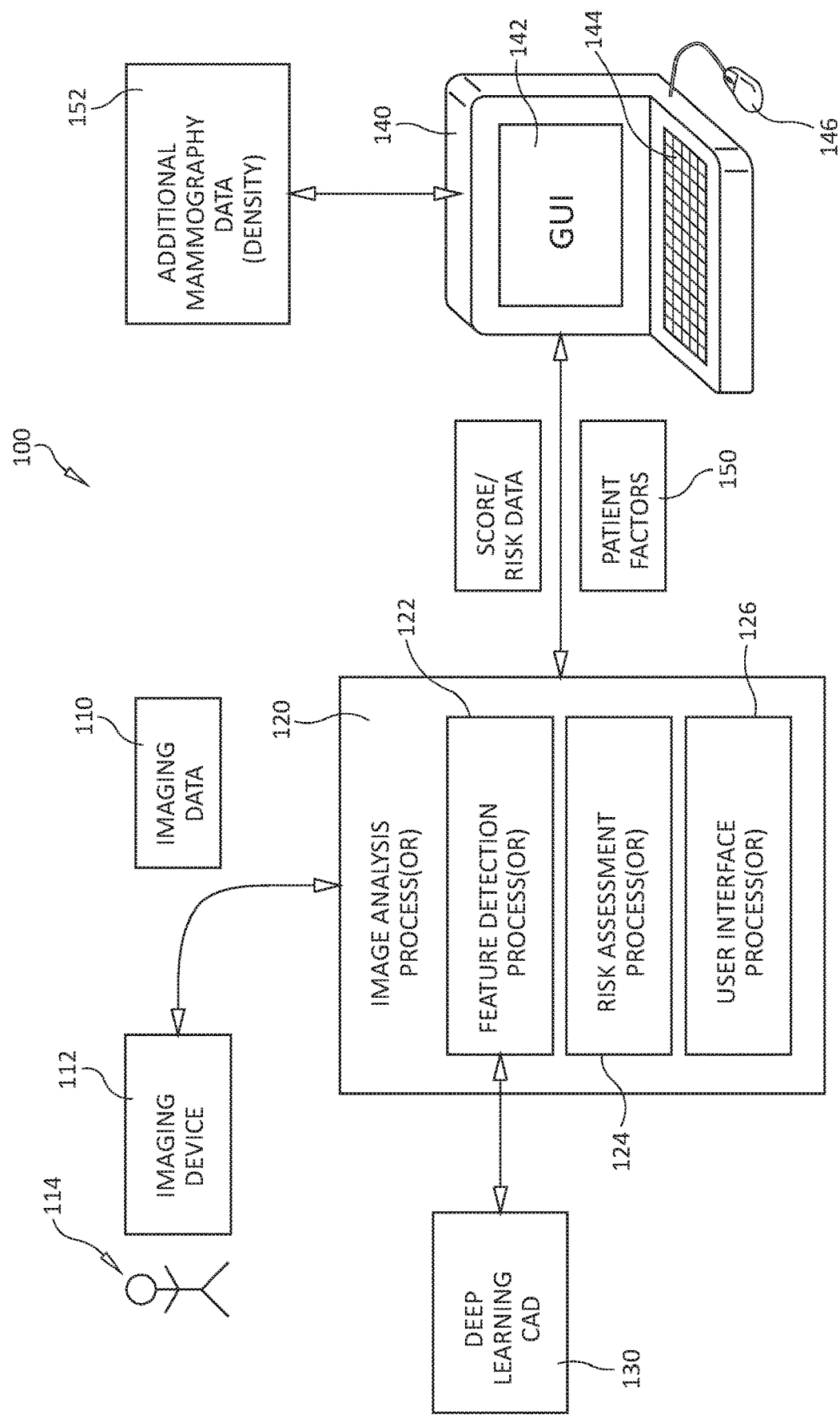
FIG. 1 is a diagram showing the delivery of breast imagery data to a processor and associated process for carrying out risk assessment and displaying results to a user/clinician in accordance with the system and method herein.

Reference is made to FIG. 1, which shows a generalized arrangement 100 in which image data 110 is derived from an imaging device 112 or store of acquired imaged—for example those acquired from a scan of a patient 114 based upon (e.g.) mammography. The image data 110 is provided to a processor and associated analysis process 120. The process(or) 120 is part of a deep learning computer-aided detection (CAD) system 130 that builds and/or employs neural networks, or similar learning arrangements/data structures (e.g. AI-based systems) to derive scores for use in evaluating the significance of detected structures within the image and underlying tissue. Note, that as used herein, the term "CAD" can refer to a computing system (hardware, software and/or firmware) that performs computer-aided detection processes, and can also (optionally) perform computer-aided analysis processes in a manner clear to those of skill. In addition, the term "CAD" can be taken to include computing systems that have been optimized for risk prediction in a manner clear to those of skill and/or in a customized manner. The process(or) can be instantiated on any acceptable computing device or environment (e.g. a laptop, PC, server, cloud, etc.) as exemplified by the device 140, which includes a display and/or touchscreen 142, keyboard 144 and mouse 146.

The process(or) 120 is provided with various factors 150, some of which are input by the user via the device 140 using an appropriate interface. These factors can include, significantly, breast/tissue density. Such density and related data can be derived from mammography delivered via the imaging device 112 or via another source, including prior, or model mammography data 152. Other data can be based upon age, previous history of cancer, lifestyle, including (e.g.) alcohol consumption, diet, smoking, drug use, sleep patterns, familial genetics, polygenic factors, etc. The processor 120 also determines the existence in the image data of (e.g.) microcalcifications. These elements are applied to a risk assessment process(or) 124 that employs a CAD score that is part of the deep learning computations.

Figure 1A:
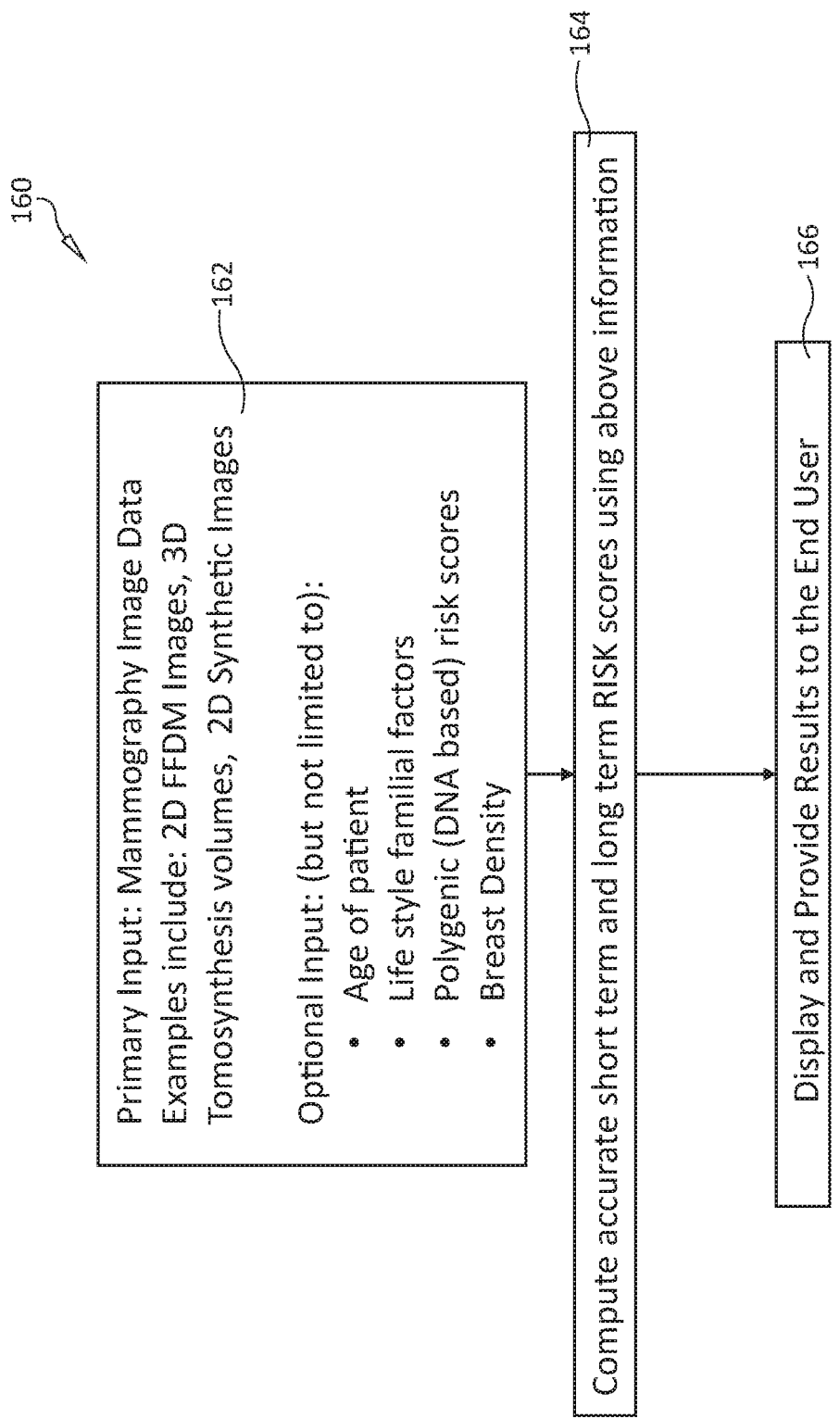
FIG. 1A is a flow diagram of an overall runtime procedure for inputting data and imagery employing the arrangement of FIG. 1.
Figure 1B:
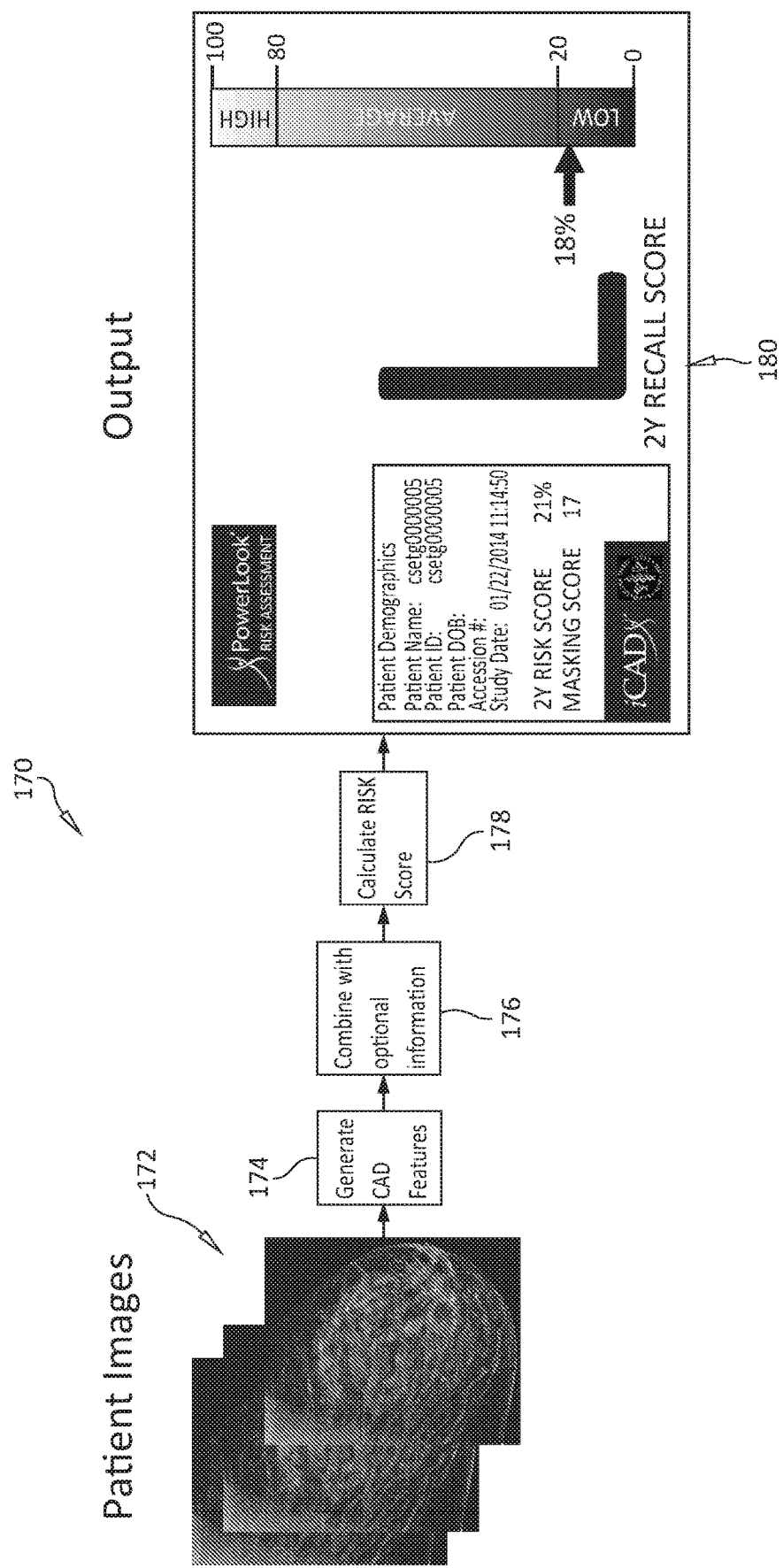
FIG. 1B is a more detailed flow diagram of the overall runtime procedure of FIG. 1B.

FIG. 1A shows a generalized runtime procedure 160 performed by, and in association with, the arrangement 100 of FIG. 1. FIG. 1B shows a graphical representation 170 of the procedure 160. As shown, in step 162, the procedure 160 inputs one or more types of mammography imagery 172 from the patient; for example, 2D FFDM images, 3D tomosynthesis volumes, and/or 2D synthetic images. The system uses this image data to compute a range of CAD features (numerical values as described below) 174. The system (for example, via interface 152) can input optional data 176 related to the patient, including, but not limited to, (a) the age of patient, (b) lifestyle familial factors, (c) polygenic (DNA based) risk factors/scores (e.g. as described in the above-referenced Karolinska study), and/or (d) breast density.

In step 164 of the overall procedure 160, the system and method herein computes accurate short term, and long-term risks scores 178 (as also described further below) using the input information from step 162. Then, in step 166, the overall procedure 160 generates and displays (and optionally stores), on (e.g.) an interface device 140, the results with associated short term and long term risk scores to the end user (e.g. a clinician, patient, etc.) based upon the computations in step 164. The display can embody a variety of formats and presentation styles—e.g. meters, bar graphs, curves and/or color-coded fields. For example, the risk score "meter" display 180 provides both a graphical and percentage display of a 2-year risk (between "low", "average", and "high") of developing a malignancy. This display 180 also includes a listed "masking score", which is described further below.

II. Score and Classifier Generation

The CAD-generated score, more particularly is employed with the following considerations:
  Breast Density plays a major factor in patient risk
  Breast Density and CAD features can be derived from mammograms
  CAD features take into account a plurality of image aspects such as:
    of suspicious findings (lesions) in the patient
    How likely these lesions are masses or microcalcifications
    How likely the masses or microcalcifications are malignant
    Texture of the breast
    Intensity distribution
  CAD features used in detection of cancers can be employed as input features for RISK prediction (process(or) 124)
  These CAD features are derived from training a CAD system to detect malignant lesions on pre-diagnostic or diagnostic mammograms.
  CAD features, along patient information such as the following are used in the prediction of the Risk score:
    factors
    Family history, and age of onset, of breast cancer
    Genetic variants, e.g. a polygenic risk score
    Age
    Body mass index
    Menopause status
    Previous history of breast tissue abnormalities
    Information from prior health care examinations
    Information on use of alcohol and tobacco
CAD features, along patient information (factors 150, described above) such as the following are used in the prediction of the Risk score in accordance with the system and method herein.

Figure 2:
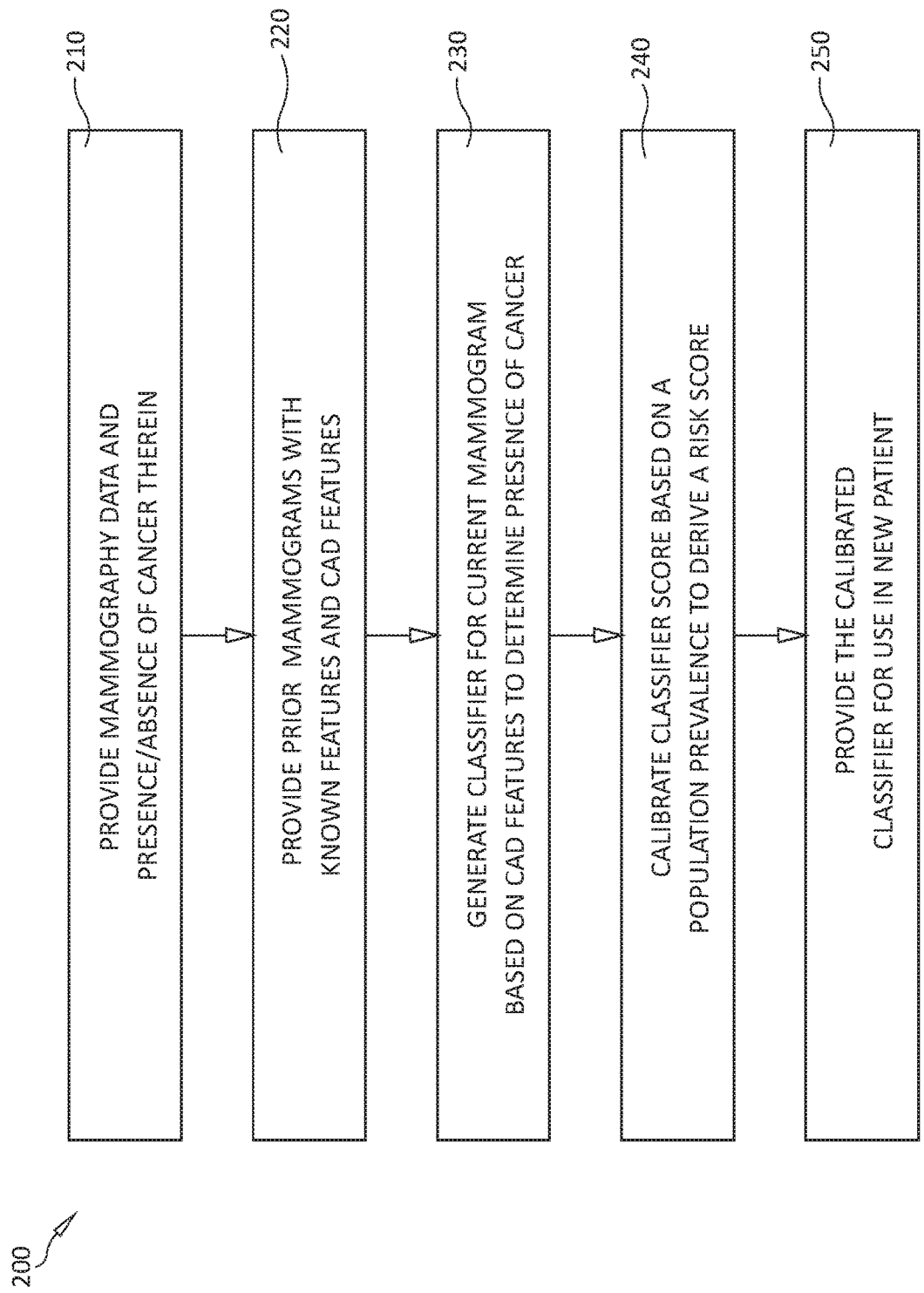
FIG. 2 is a flow diagram showing the generation/training of a calibrated classifier from patient mammography data for use in runtime risk assessment processes.

Reference is now made to the procedure 200 of FIG. 2, in which the above information is used by the risk assessment module/process 134 to derive a risk score. In step 210, a set of mammograms and their priors are provided for the patient. The data includes knowledge as to whether the current mammogram contains cancer. In step 220 prior mammograms with known features including CAD features computed on the images are also provided to the procedure 200. In step 230, and based upon the present and prior mammogram data, the procedure 200 designs/generates a classifier to predict if the current mammogram of the same patient contains cancer or not. In step 240, the classifier score is then calibrated based on a population prevalence to derive a risk score.

Figure 2A:
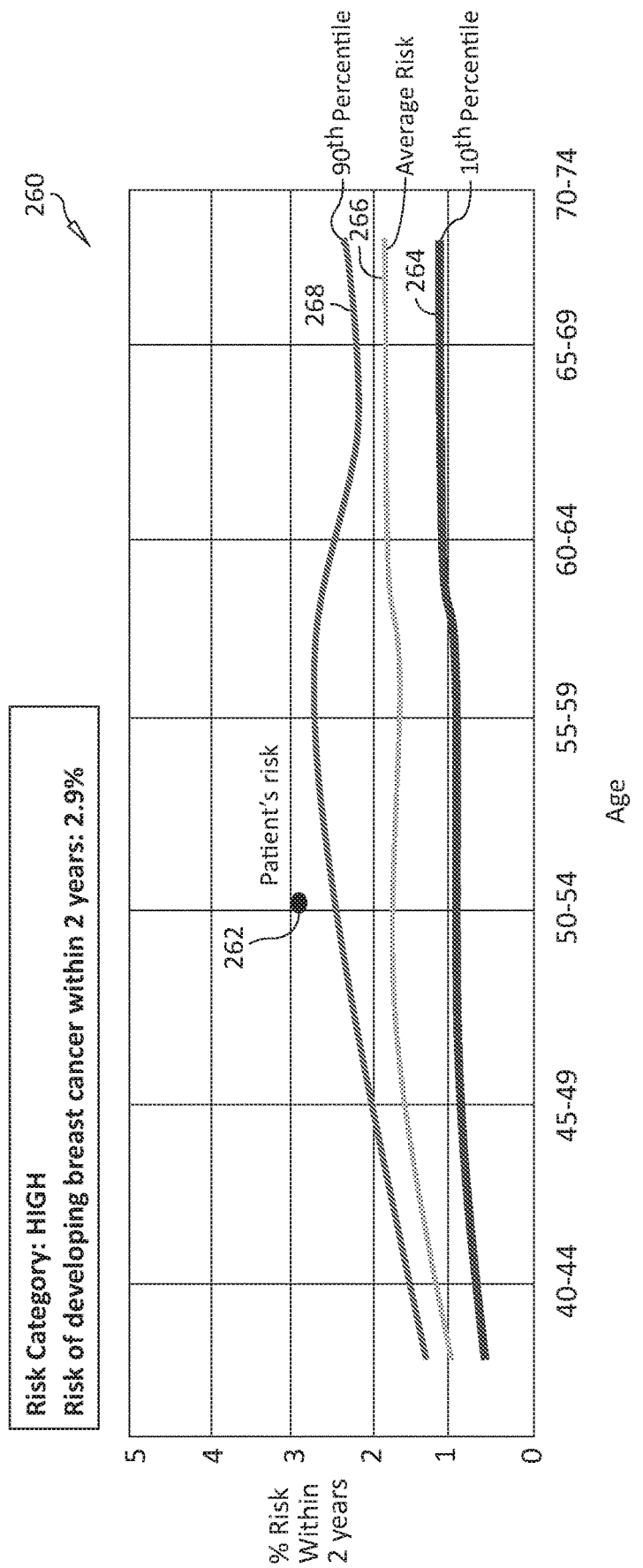
FIG. 2A is an exemplary graph showing patient cancer risk at a single time point versus population prevalence over a range of ages for use in risk assessment and training in accordance with the system and method.
Figure 2B:
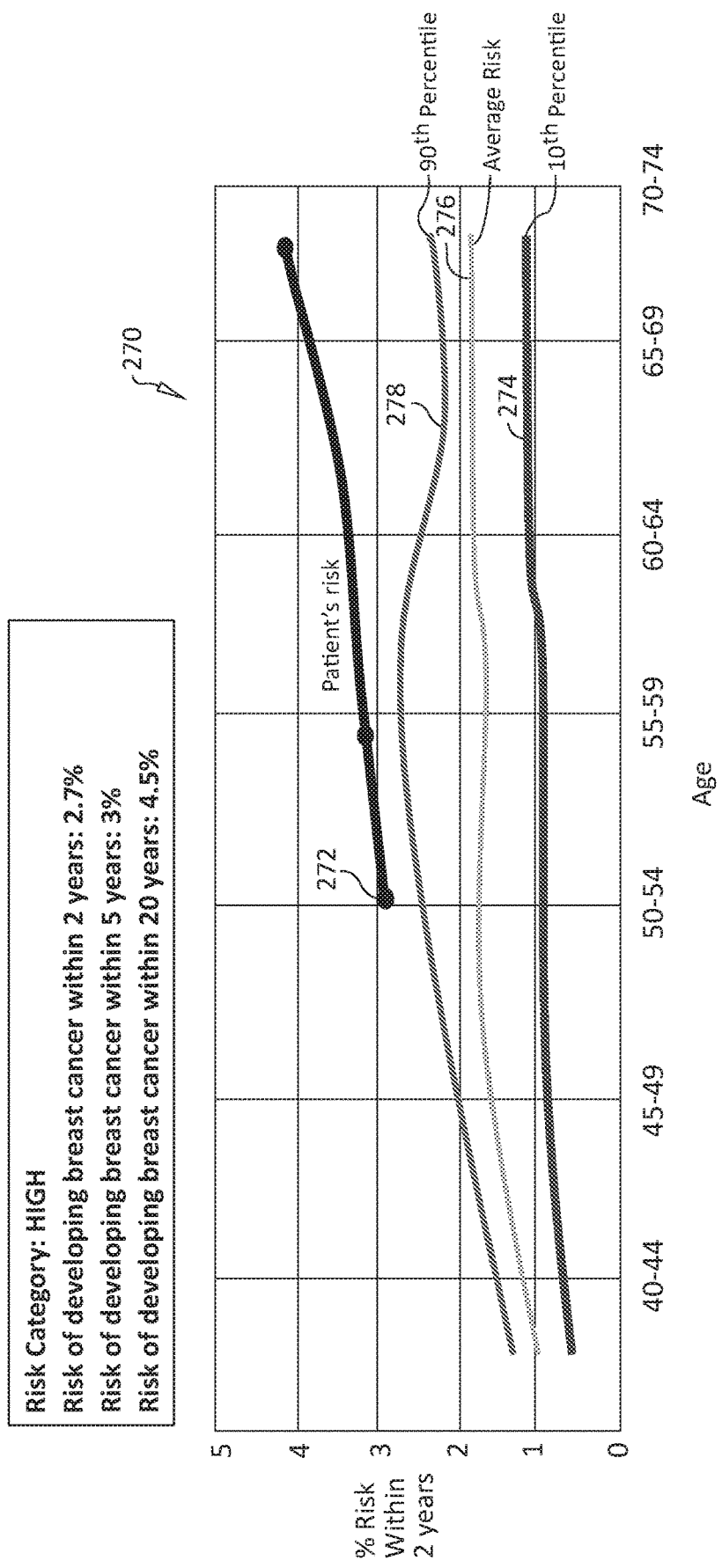
FIG. 2B is an exemplary graph showing patient cancer risk over time versus population prevalence over a range of ages for use in risk assessment and training in accordance with the system and method.

With reference now to FIGS. 2A and 2B, respective graphs 260 and 270 are provided, showing a plot 262 and 272 the age-related risk for a patient of developing breast cancer versus a general population's risk at a given age range. The curves for population prevalence in these examples represent a risk of 10-percent (264, 274), average (266, 276) and 90-percent (268, 278). The plot 272 of patient risk is extended over 20 years in graph 270.

By way of further background, CAD is designed to detect malignant lesions, such as microcalcifications and masses occurring in (e.g.) breast tissue. In the present system and method, the features computed as part of this process take into consideration (a) the number of suspicious findings (lesions) in the patient, (b) how likely these lesions are masses or microcalcifications, (c) how likely the masses and microcalcifications are malignant, (d) the relative distribution in the left and right breast, (e) the relative texture of the breast tissue and (f) the relative intensity distribution within the acquired image. These features are mapped to respective numerical values for each detection event. In one example, the CAD features can be characterized by approximately 65 floating-point values. Hence, by providing a large number of variable features, the overall accuracy of the computed short term and long term risk model can be substantially improved over prior techniques.

Figure 3:
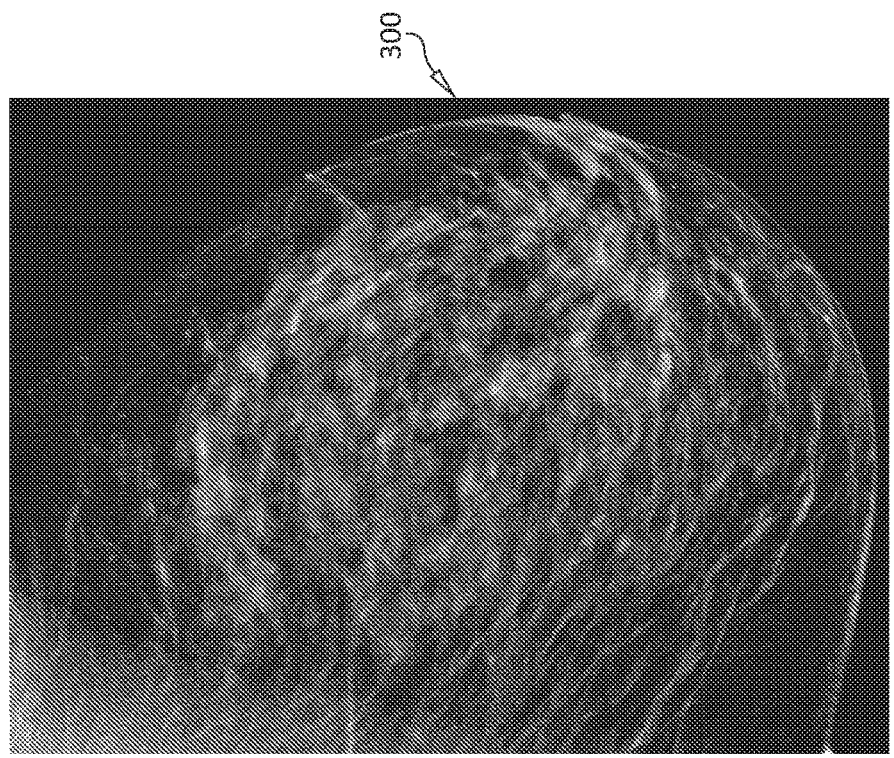
FIG. 3 is an exemplary acquired/input image of a breast for runtime analysis by the CAD system in accordance with the system and method.
Figure 3A:
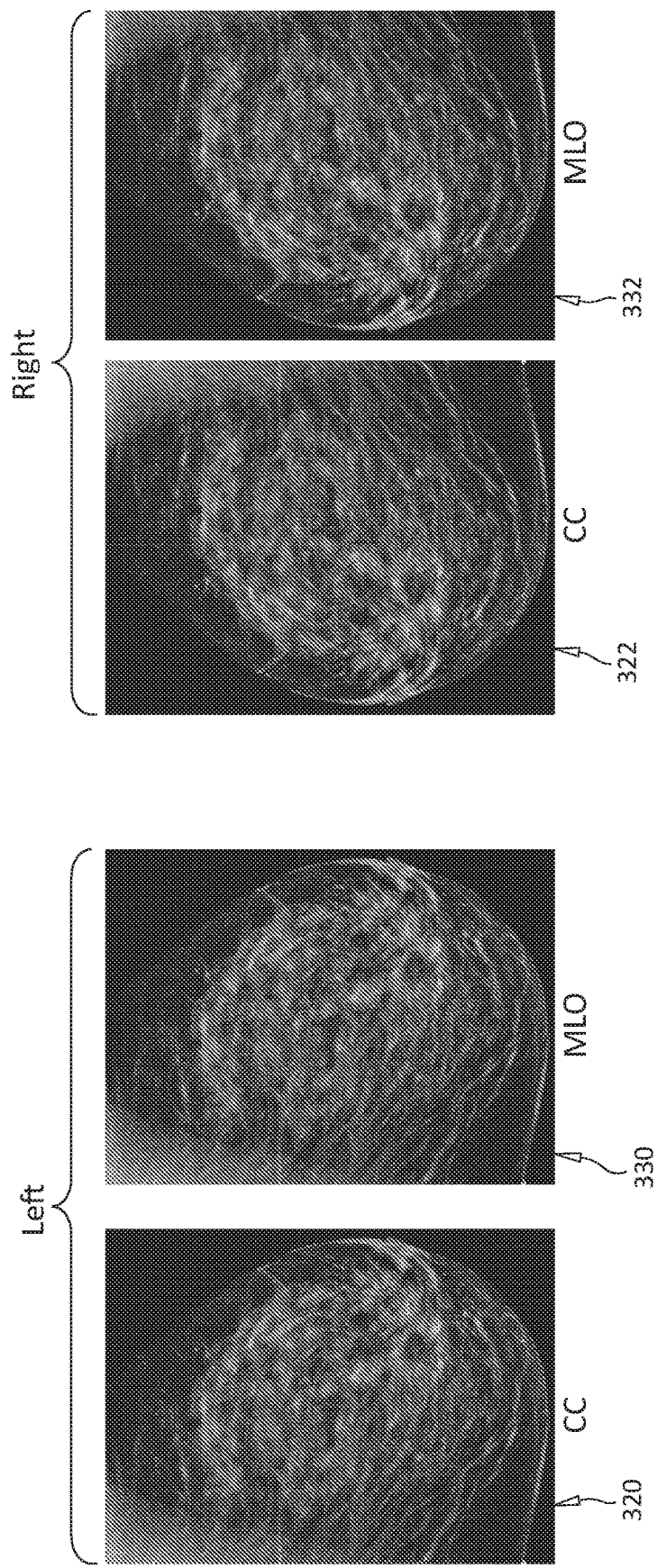
FIG. 3A is an exemplary set of left breast and right breast images for input to the CAD system in accordance with FIG. 3.
Figure 4:
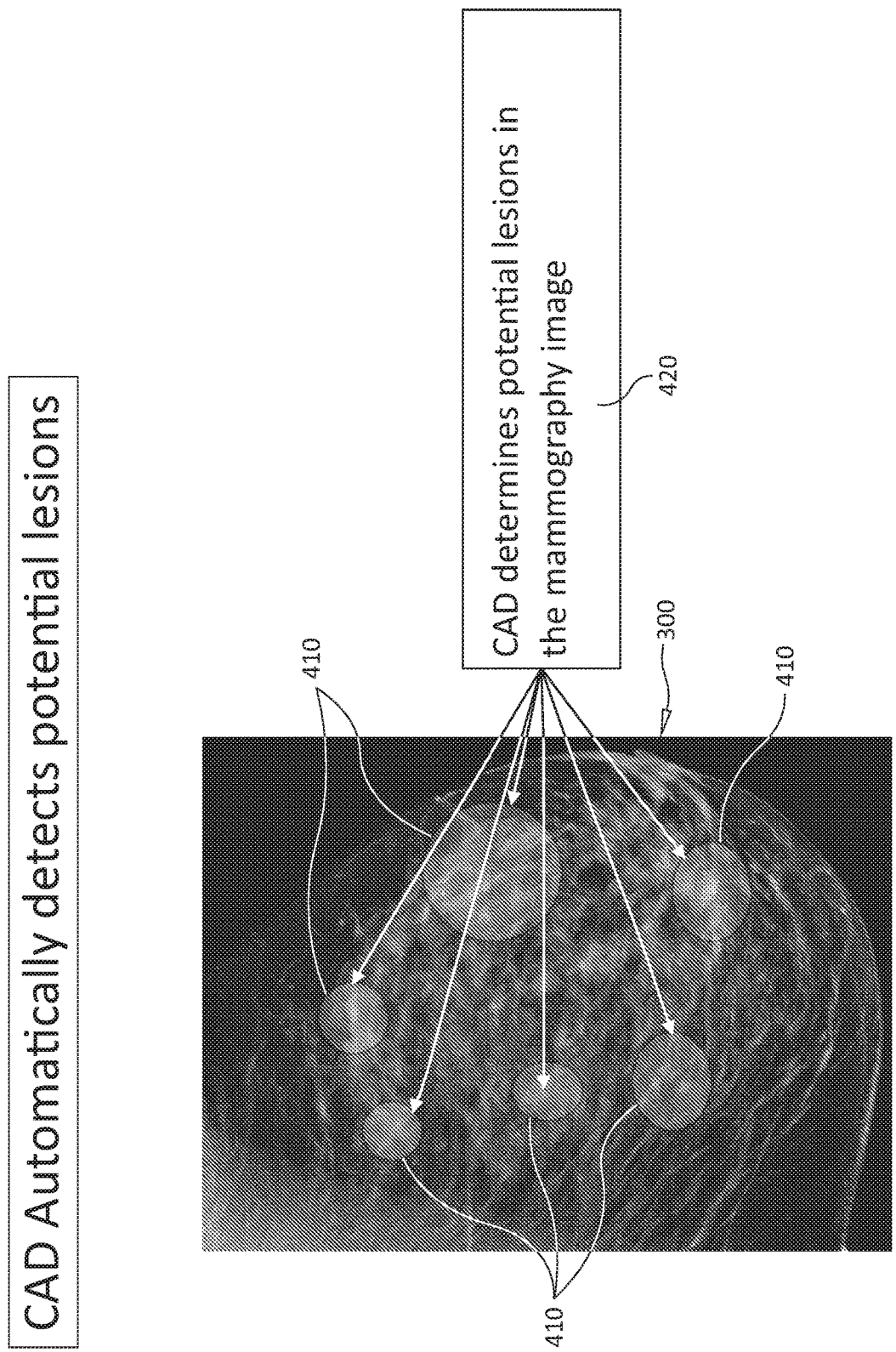
FIG. 4 is an exemplary image of the breast according to FIG. 3 showing the identification and location of candidate lesions in the tissue for further analysis by the CAD system.
Figure 5:
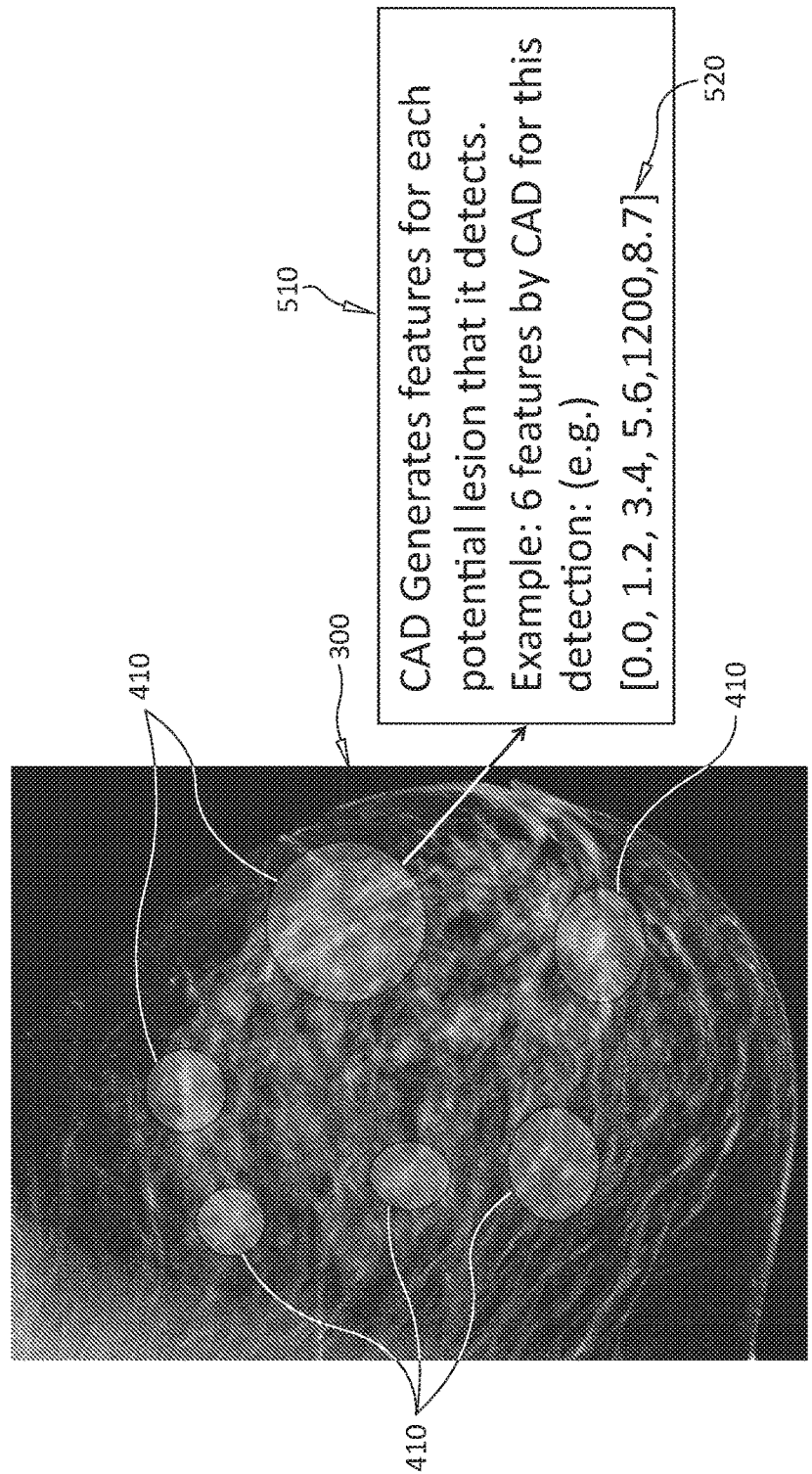
FIG. 5 is an exemplary image of the breast according to FIG. 3 showing the computation of feature values based on the identification and location of candidate lesions by the CAD system according to FIG. 4.

With reference to FIGS. 3-5, the process for computing feature values is depicted in view of an input image 300 (FIG. 3) of a breast. In an exemplary embodiment, shown in FIG. 3A, the imagery can include both craniocaudal (CC) 320 and 322 and mediolateral oblique (MLO) 330 and 332 views of respective left and right breasts. The CAD system analyzes (block 420) the image(s) 300 using commercially available/known techniques, and generates a list with locations 410 of potential malignant lesions. After locating potential lesions 410, the CAD system then generates feature numerical values 520 for each of these respective lesions (block 510 in FIG. 5), again, using available and known techniques.

Note that in step 250, the calibrated classifier can be provided to a follow-on runtime process for use with a new patient. As such, mammography images related to the new patient are input to the risk assessment process, with associated patient information/factors. This information is then used to output the predicted risk score.

III. Results Presentation

Figure 6:
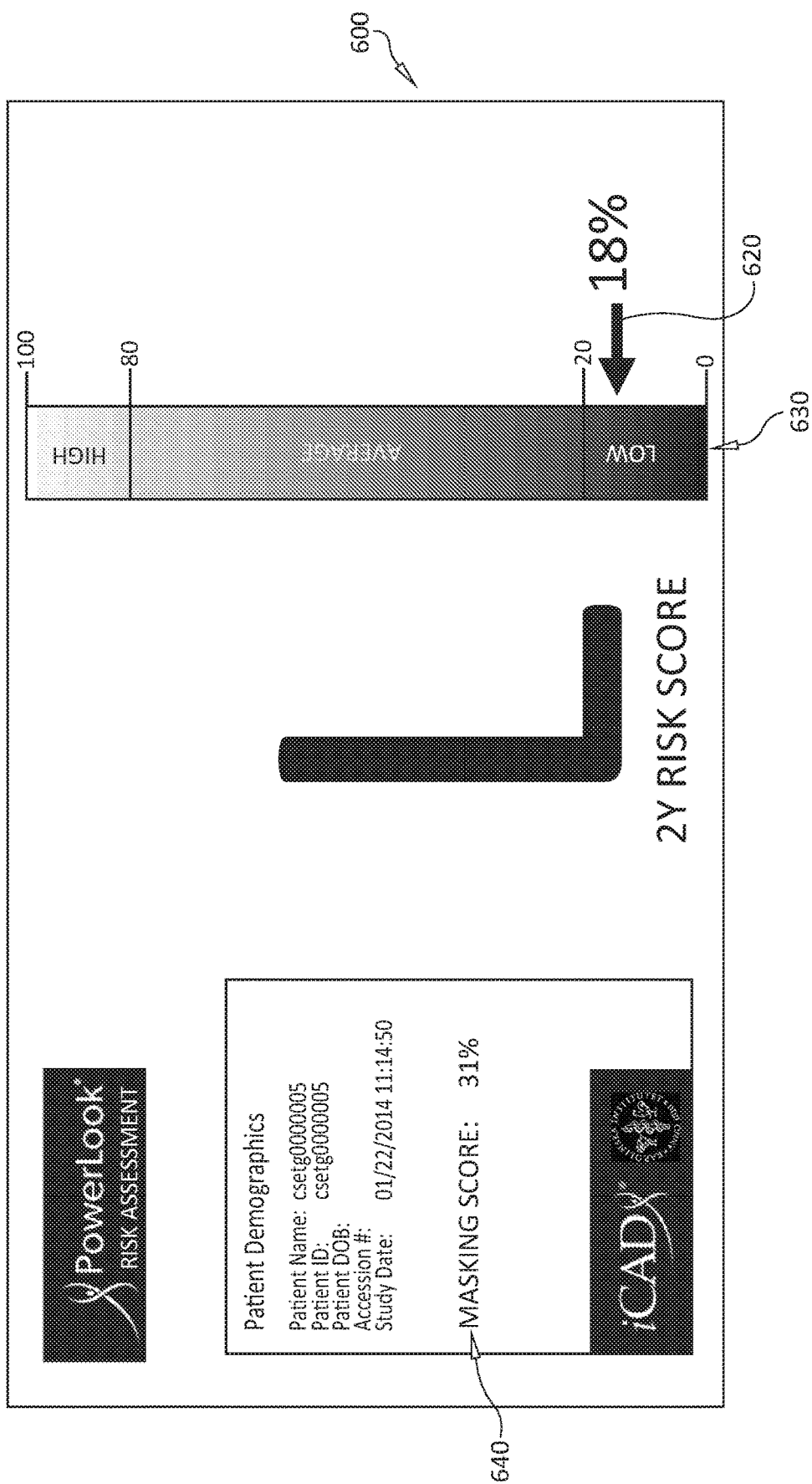
FIGS. 6-8 are exemplary displays presented to a user by the system and method showing risk and recall scores graphically and as a percentage value.
Figure 7:
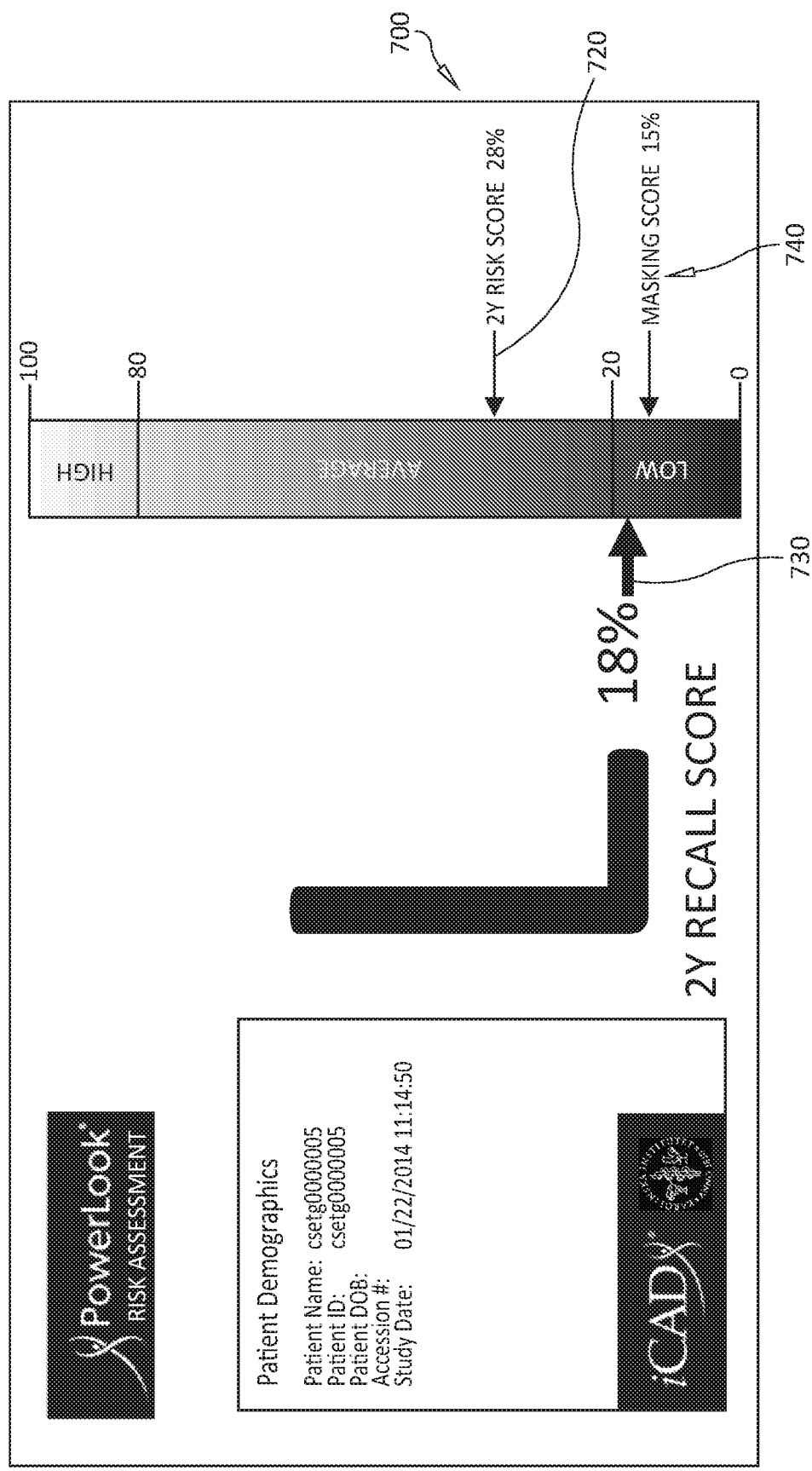
Figure 8:
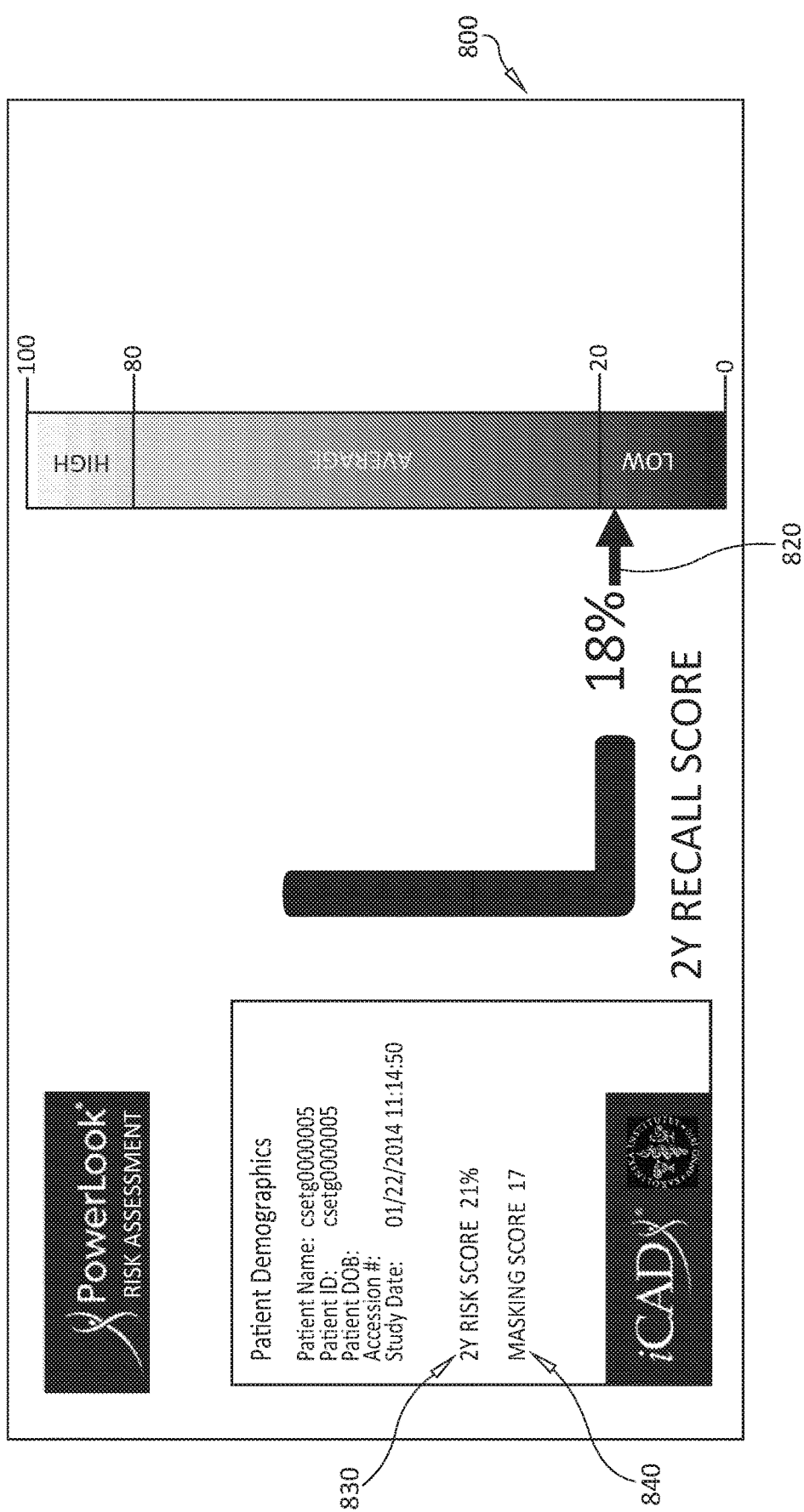

The process(or) 120 (FIG. 1) includes a user interface and/or GUI driving component 126. This is used to generate displays for use by the clinician, or others to visualize the risk computed from the information provided. The results of the above-described procedures and computations can, thus, be displayed to a user and/or clinician for use in advising patients and guiding follow-up visits and treatment. Some examples of exemplary displays are shown in FIGS. 6-8. In the display 600 of FIG. 6, a 2-year risk score for a patient (e.g. 18 percent of developing breast cancer) is shown using a pointer 620 associated with a vertical (e.g. color or intensity-coded) bar graph 630. The exemplary display 700 in FIG. 7 provides a pointer 720 for 2-year risk score (e.g. 28%) and also a 2-year recall score pointer 730 (e.g. 18%). In the display 800, the recall score is provided as a pointer 820, while the 2-year recall score 830 is listed alphanumerically only.

Note that the actual depicted risk value(s) and range can be highly variable in exemplary implementations. For example, instead of a 0-100 scale, the overall scale between approximately 0% and 2% (or another relatively low, maximum percentage). In such an example, the depicted "LOW" risk value can end at approximately 0.15%; the "AVERAGE" risk can end at approximately 0.6%; the depicted "HIGH" risk can end at approximately 1.6%; and the depicted "HIGH+" (very high) risk can extend above 1.6% to a maximum of 2, or more, percent. The overall scale, and values selected for each level, can be computed based upon the various factors described herein. There can be predetermined thresholds that such computations use to scale the risk levels.

It is contemplated that the risk assessment process 124 can compute a masking score, which is also depicted alphanumerically (640 and 840) in exemplary displays 600 and 800, and with a pointer 740 in display 700. The masking score calculates a particular metric that quantifies risk in situations where the patient carries a high probability for a tumor and a low probability of that tumor being detected within the current examination. The masking score is trained on breast cancer cases using the risk score determinants and additionally on mode-of-detection (interval cancer vs. screen-detected cancers). The score identifies specific image features and patient characteristics that differ between interval and screen-detected cancers. A predicted high masking score typically translates into a high probability for interval cancers. More generally, the system's risk assessment module can receive score data from prior imagery of the patient's tissue to allow monitoring of a therapy response by a clinician.

Note that it is desirable for the clinician to monitor patients at predetermined intervals for any changes in risk score and masking score due to their response to therapy. In this manner, the clinician can then suggest any appropriate changes in the individualized program for that patient.

The risk assessment process 124 can compute a "recall" score, which is also depicted alphanumerically (630 and 820) in exemplary displays 600 and 800, and with a pointer 730 in display 700. The recall score is a computer-aided indicator for recommending an individualized healthcare program to the patient.

By way of example, reference is made to the UK NICE guidelines (https://www.nice.org.uk/guidance/cg164). An extract of the NICE guidelines health care program for (e.g.) women at high risk of breast cancer is listed below:

1.6.2 Do not routinely offer ultrasound surveillance to women at moderate or high risk of breast cancer but consider it:
when MRI surveillance would normally be offered but is not suitable (for example, because of claustrophobia)
when results of mammography or MRI are difficult to interpret.
1.6.3. Offer annual mammographic surveillance to women:
aged 40-49 years at moderate risk of breast cancer
aged 40-59 years at high risk of breast cancer but with a 30% or lower probability of being a BRCA or TP53 carrier
aged 40-59 years who have not had genetic testing but have a greater than 30% probability of being a BRCA carrier
aged 40-69 years with a known BRCA1 or BRCA2 mutation. [2013]

REF https://www.nice.org.uk/guidance/cg164/chapter/Recommendations#surveillance-and-strategies-for-early-detection-of-breast-cancer.

The characterization of the recall score is based upon the risk score and the masking score. A higher risk-score indicates that the patient is at higher risk for being diagnosed with breast cancer. A higher masking score indicates that the patient is at higher risk, and that the results of the modality (e.g. digital mammography) are difficult to interpret. A higher recall score further indicates that the patient is at higher risk and/or have a higher masking probability. The recall score is a statistical construct upon the risk and masking scores. The range of the recall score is defined between 0% and 100% and cut-offs on the scale defines categories. The categories are used to indicate a recommendation for an individualized health care program to the woman. Examples of recommendations are following up current exam using a modality with increased sensitivity, follow-up for suspicion of cancer, participating in a program to decrease breast cancer risk or masking, more intense screening or less frequent screening.

IV. Performance

The following table shows at least a 7% improvement in AUC for the curve of sensitivity versus specificity with the system and method (Model 1), which incorporates CAD detection features into the risk model proffered in the Karolinska study. Other Models further improving the accuracy and traditional risk models are also depicted by way of comparison.

| | Discrimination performance AUC (95% CI)[1] | | |
|---|---|---|---|
| Model | Recall score[2] | Risk | Masking effect |
| 1. Mammographic density, microcalcifications, masses, age | 0.77 (0.74-0.80) | 0.72 (0.71-0.75) | 0.80 (0.78-, 0.83) |
| 2. Model 1 + lifestyle and familial risk factors[3] | 0.77 (0.74-0.80) | 0.73 (0.71-0.76) | 0.80 (0.78-0.83) |
| 3. Model 2 + PRS | 0.79 (0.76-0.82) | 0.75 (0.72-0.78) | 0.80 (0.78-0.83) |
| Comparison to other risk models: | | | |
| PRS (BCAC) | | 0.65 (0.62-0.67) | |
| Tyrer-Cuzick | | 0.63 (0.61-0.65) | |
| Gail | | 0.55 (0.53-0.57) | |

[1]Discrimination performance using area under the receiver-operating curve (AUC) and 95% confidence intervals.
[2]Recall score contrasted incident breast cancer cases with controls using the risk score and masking score as predictors. The risk and masking scores were predicted on the full cohort with time frames from the risk and masking projection respectively.
[3]The included lifestyle and familial risk factors were BMI, menopause status, current use of HRT, tobacco, alcohol, and family history of breast cancer.

The Hosmer-Lemeshow model fit test statistic for recall models 1, 2, and 3 were 0.22, 0.16, and 0.24.

V. Conclusion

It should be clear that the above-described system and method for modelling risk based upon CAD analysis of image data in combination with patient information and traditional factors (breast density) achieves a substantial improvement in the accuracy of the results. This approach allows for learning to improve the overall model through progressive update of existing image data through a CAD-based (e.g. deep learning, neural network, AI) computational environment. The results can be displayed in a variety of graphical formats that increase the ease of understanding for users and patients.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A computing system processor for assessing risk of being diagnosed with cancer based upon imagery of tissue and patient-related factors, the system comprising:
   a computer-aided detection (CAD) or AI-based program stored in non-transient computer memory that is accessible to the computing system processor that when executed by the processor analyzes the imagery and generates a set of floating point numerical feature values characterizing the imagery of tissue;
   an assessment module executing on the computing system processor and including a classifier that is: (i) generated based on the imagery of tissue for a patient and at least one prior set of imagery of tissue for the patient, (ii) calibrated based on a population prevalence of age-based risk for cancer to derive a risk score, and (iii) configured to predict presence of at least one cancerous tissue in the imagery of tissue for the patient, the risk score indicating a risk of the patient developing cancer that is characterized by a low probability of detection, the risk score further based upon a plurality of distinct image features and corresponding floating point numerical feature values; and
   an output module that when executed on the computing system processor provides an output of the risk score versus a scale of risk scores.

2. The system as set forth in claim 1 wherein the assessment module receives score data from prior imagery of tissue for monitoring a therapy response by a clinician.

3. The system as set forth in claim 1 wherein the assessment module receives score data from prior imagery of tissue for monitoring a therapy response by a clinician.

4. The system as set forth in claim 1, further comprising a masking score generator module that receives inputs from the patient factors and history, and computes the risk of having a cancer characterized by a low probability of detection, based upon the feature values and the patient factors and history.

5. The system as set forth in claim 4 wherein the assessment module receives score data from prior imagery of tissue for monitoring a therapy response by a clinician.

6. The system as set forth in claim 4, further comprising a recall determination module that receives inputs from the assessment module and the masking score generator module, and generates a computer-aided indication of a recommended clinical follow-up for the patient.

7. The system as set forth in claim 4, further comprising a user interface output module that provides a graphical display of an output of the masking score generator versus a scale of masking values.

8. The system as set forth in claim 7 wherein the display output provides a recall score.

9. The system as set forth in claim 1 wherein the assessment module receives score data from prior imagery of tissue that is verified to include cancer by a specialist.

10. The system as set forth in claim 1 wherein the patient-related factors include at least one of (a) breast imagery, (b) percent tissue density, (c) density compactness, (d) age when the imagery is acquired, (e) BMI, (f) menopause status, (g) family history of cancer, (h) personal history of disease, (i) lifestyle factors, (j) genetic variants, and (k) information from prior health care examinations.

11. The system as set forth in claim 1 wherein the assessment module determines cancer of a specific subtype or generalized breast cancer.

12. The system as set forth in claim 11 wherein the features are established based upon lesion candidates localized in the tissue by the CAD system.

13. The system as set forth in claim 12, wherein the assessment module employs differences between each breast side for microcalcifications, masses and the tissue density.

14. The system as set forth in claim 13 wherein the assessment module employs an interaction between tissue density and masses.

15. The system as set forth in claim 1 further comprising a user interface output module that provides a graphical display output of the risk versus a scale of risk values.

16. The system as set forth in claim 1 wherein the tissue is human breast tissue and the imagery is mammography imagery.

17. The system as set forth in claim 1, further comprising, a masking score generator module trained on cancerous tissue imagery and a mode of cancer detecting including at least one of interval cancer and screen-detected cancer, the masking score generator identifying at least one or more image features of the imagery of tissue or patient-related factors that differ between interval and screen-detected cancers.

18. A method for assessing risk of being diagnosed with cancer based upon imagery of tissue and other patient-related factors, the method comprising the steps of:

analyzing, with a computer-aided detection (CAD) or AI-based computer system, the imagery of tissue and generating with a processor a set of floating point numerical feature values characterizing the imagery of tissue;

deriving a risk score with a classifier generated based on the imagery of tissue for a patient and at least one prior set of imagery of tissue for the patient, wherein the classifier is calibrated based on a population prevalence of age-based risk for cancer, the risk score indicating a risk of the patient developing cancer characterized by a low probability of detection, the risk score further based upon a plurality of distinct image features, corresponding floating point numerical feature values and the patient-related factors and history; and predicting, with the classifier, presence of at least one cancerous tissue in the imagery of tissue for the patient.

19. The method as set forth in claim 18, further comprising determining a recall score, and generating, based on the recall score a computer-aided indication of a recommended clinical follow-up for the patient.

20. The method as set forth in claim 18, further comprising identifying, with a masking score generator module trained on cancerous tissue imagery and a mode of cancer detecting including at least one of interval cancer and screen-detected cancer, at least one or more image features of the imagery of tissue or patient-related factors that differ between interval and screen-detected cancers.

* * * * *